United States Patent
Rosen et al.

[11] Patent Number: 5,919,983
[45] Date of Patent: Jul. 6, 1999

[54] HIGHLY SOLUBLE OLEFIN POLYMERIZATION CATALYST ACTIVATOR

[75] Inventors: Robert K. Rosen; Daniel D. VanderLende, both of Sugar Land, Tex.

[73] Assignee: The Dow Chemical Company, Midland, Mich.

[21] Appl. No.: 08/818,530

[22] Filed: Mar. 14, 1997

Related U.S. Application Data

[XX .
[60] Provisional application No. 60/014,284, Mar. 27, 1996.
[51] Int. Cl.$^6$ ................................. C07F 5/02; C07F 9/02
[52] U.S. Cl. .................. 568/3; 568/6; 568/2; 568/14; 568/16; 568/27; 568/74; 502/152; 526/132; 526/133; 526/134
[58] Field of Search .................................. 568/3, 12, 16, 568/74, 2, 6, 14, 27

[56] References Cited

U.S. PATENT DOCUMENTS

| | | |
|---|---|---|
| 4,246,259 | 1/1981 | Kathawala ................................. 568/74 |
| 4,543,399 | 9/1985 | Jenkins, III et al. . |
| 4,564,647 | 1/1986 | Hayashi et al. . |
| 4,588,790 | 5/1986 | Jenkins, III et al. . |
| 5,032,652 | 7/1991 | Chang . |
| 5,084,534 | 1/1992 | Welborn et al. . |
| 5,132,380 | 7/1992 | Stevens et al. . |
| 5,153,157 | 10/1992 | Hlatky et al. . |
| 5,198,401 | 3/1993 | Turner et al. . |
| 5,405,922 | 4/1995 | DeChellis et al. . |
| 5,447,895 | 9/1995 | Marks et al. . |
| 5,468,902 | 11/1995 | Castellanos et al. ...................... 568/74 |
| 5,470,927 | 11/1995 | Turner et al. . |
| 5,489,659 | 2/1996 | Sugano et al. ........................... 526/132 |
| 5,559,199 | 9/1996 | Abe et al. ................................ 526/134 |
| 5,576,259 | 11/1996 | Hasegawa et al ....................... 526/132 |
| 5,629,398 | 5/1997 | Okamoto et al. ....................... 526/132 |

FOREIGN PATENT DOCUMENTS

| | | |
|---|---|---|
| 88/02009 | 3/1988 | WIPO . |
| 94/00500 | 1/1994 | WIPO . |

*Primary Examiner*—Edward J. Smith

[57] ABSTRACT

A catalyst activator, comprising a cation which is a Bronsted acid capable of donating a proton, and an inert, compatible, noncoordinating, anion, characterized by a solubility constant at 25° C. in hexane, cyclohexane or methylcyclohexane of at least 5 weight percent.

7 Claims, No Drawings

HIGHLY SOLUBLE OLEFIN POLYMERIZATION CATALYST ACTIVATOR

CROSS-REFERENCE TO RELATED APPLICATION

This application claims the benefit of U.S. Provisional Application No. 60/014,284, filed Mar. 27, 1996.

BACKGROUND OF THE INVENTION

The present invention relates to a catalyst activator. More particularly the present invention relates to a catalyst activator particularly adapted for use in a solution polymerization process for polymerization of α-olefins. Such an activator is particularly advantageous for use in a continuous solution polymerization process wherein catalyst, catalyst activator, and at least one polymerizable monomer are continuously added to a reactor operating under solution polymerization conditions, and polymerized product is continuously removed therefrom.

It is previously known in the art to activate Ziegler-Natta polymerization catalysts, particularly such catalysts comprising Group 4 metal complexes containing delocalized π-bonded ligand groups, by the use of Bronsted acid salts capable of transferring a proton to form a cationic derivative of such Group 4 metal complex. Preferred Bronsted acid salts are such compounds containing a noncoordinating anion that is capable of stabilizing the resulting Group 4 metal cation, especially tetrakis(pentafluorophenyl)borate. Examples of such Bronsted acid salt activators, which are a species of ionic activator, are protonated ammonium, sulfonium, or phosphonium salts disclosed in U.S. Pat. No. 5,198,401, U.S. Pat. No. 5,132,380, U.S. Pat. No. 5,470,927, and U.S. Pat. No. 5,153,157.

Due to the fact that such activators are fully ionized and the corresponding anion is highly noncoordinating, such activators are extremely effective as olefin polymerization catalyst activators. Disadvantageously, however, because they are ionic salts, such activators are extremely insoluble in aliphatic hydrocarbons and only sparingly soluble in aromatic solvents. It is desirable to conduct most polymerizations of α-olefins in aliphatic hydrocarbon solvents due to the compatibility of such solvents with the monomer and in order to reduce the aromatic hydrocarbon content of the resulting polymer product. Normally, ionic salt activators need to be added to such polymerizations in the form of a solution in an aromatic solvent such as toluene. The use of even a small quantity of such an aromatic solvent for this purpose is undesirable since it must be removed in a devolatilization step and separated from other volatile components, a process that adds significant cost and complexity to any commercial process. In addition, the foregoing ionic cocatalysts often exist in the form of an oily, intractable material which is not readily handled and metered or precisely incorporated into the reaction mixture.

Accordingly, it would be desirable if there were provided an ionic catalyst activator that could be employed in solution polymerizations that use an aliphatic solvent, including condensed α-olefin monomer. In addition it would be desirable to provide a new form of ionic catalyst activator that is particularly adapted for use in a continuous solution polymerization reaction where controlled addition of specific quantities of such activator is required.

SUMMARY OF THE INVENTION

According to the present invention there is now provided a catalyst activator, comprising a cation which is a Bronsted acid capable of donating a proton, and an inert, compatible, noncoordinating, anion, characterized by a solubility at 25° C. in hexane, cyclohexane or methylcyclohexane of at least 5 weight percent, preferably at least 7.5 weight percent.

Additionally according to the present invention there is provided a solution polymerization of an α-olefin comprising contacting one or more α-olefins, optionally in the presence of an inert aliphatic, alicyclic or aromatic hydrocarbon, with a catalyst system comprising the above described catalyst activator.

By the use of the foregoing catalyst activator, improved catalyst activation is provided. More particularly, increased catalyst efficiency and rate of polymerization are obtained, especially under solution polymerization conditions, most especially continuous, solution polymerization conditions.

DETAILED DESCRIPTION OF THE INVENTION

All references herein to elements belonging to a certain Group refer to the Periodic Table of the Elements published and copyrighted by CRC Press, Inc., 1989. Also any reference to the Group or Groups shall be to the Group or Groups as reflected in this Periodic Table of the Elements using the IUPAC system for numbering groups.

The catalyst activators of the invention are further characterized in the following manner. Preferred anions are those containing a single coordination complex comprising a charge bearing metal or metalloid core which anion is capable of balancing the charge of the active catalyst species (the metal cation) which is formed when the two components are combined. Also, said anion should be sufficiently labile to be displaced by olefinic, diolefinic and acetylenically unsaturated compounds or neutral Lewis bases such as ethers, amines or nitrites. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially. Therefore, said single boron atom compounds are preferred.

Preferably the cocatalysts of the invention may be represented by the following general formula: $(L^*-H)_d^+(A^{d-})$, wherein:

L* is a neutral Lewis base;

$(L^*-H)^+$ is a Bronsted acid;

$A^{d-}$ is a noncoordinating, compatible anion having charge d−, and d is an integer from 1 to 3.

Examples of suitable anions of the formula $A^{d-}$ include sterically shielded diboron anions corresponding to the formula:

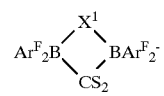

wherein:

S is alkyl, fluoroalkyl, aryl, or fluoroaryl (and where two S groups are present additionally hydrogen), $Ar^F$ is fluoroaryl, and $X^1$ is either hydrogen or halide.

Such diboron anions are disclosed in U.S. Pat. No. 5,447,895, the teachings of which are herein incorporated by reference.

Additional examples of $A^{d-}$ anions are those anions corresponding to the formula: $[M'^{k+}Q_{n'}]^{d-}$, wherein:

k is an integer from 1 to 3;
n' is an integer from 2 to 6;
n'−k=d;
M' is an element selected from Group 13 of the Periodic Table of the Elements; and
Q independently each occurrence is selected from hydride, dialkylamido, halide, alkoxide, aryloxide, hydrocarbyl, and halosubstituted-hydrocarbyl radicals, said Q having up to 20 carbons with the proviso that in not more than one occurrence is Q halide.

In a more preferred embodiment, d is one, that is, the counter ion has a single negative charge and corresponds to the formula, $A^-$. Activating cocatalysts comprising boron which are particularly useful in this invention may be represented by the following general formula: $[L*-H]^+ [BQ'_4]^-$, wherein:

L* is a nitrogen, sulfur or phosphorus containing neutral Lewis base;
B is boron in an oxidation state of 3; and
Q' is a fluorinated $C_{1-20}$ hydrocarbyl group.

Most preferably, Q' is in each occurrence a fluorinated aryl group, especially a pentafluorophenyl group.

Generally, solubility of the catalyst activators of the invention in aliphatic compounds is increased by incorporation of one or more oleophilic groups such as long chain alkyl groups; long chain alkenyl groups; or halo-, alkoxy-, amino-, silyl-, or germyl-substituted long chain alkyl groups or long chain alkenyl groups into the Bronsted acid, L. By the term "long chain" are meant groups having from 10 to 50 non-hydrogen atoms in such group, preferably in a non-branched form. Preferably such L groups contain from 1 to 3 $C_{10-40}$ n-alkyl groups with a total of from 12 to 100 carbons, more preferably 2 $C_{10-40}$ alkyl groups and from 21 to 90 total carbons. The presence of such oleophilic groups is believed to render the activator more soluble in aliphatic liquids thereby improving the effectiveness in catalyst activation. It is understood that the catalyst activator may comprise a mixture of oleophilic groups of differing lengths. For example, one suitable activator is the protonated ammonium salt derived from the commercially available long chain amine comprising a mixture of two $C_{14}$, $C_{16}$ or $C_{18}$ alkyl groups and one methyl group. Such amines are available from Witco Corp., under the trade name Kemamine™ T9701, and from Akzo-Nobel under the trade name Armeen™ M2HT. The present cocatalysts may be used in reduced concentrations based on amount of metal complex compared to the amounts of prior known cocatalysts previously required, while retaining equivalent or improved catalyst efficiencies.

Illustrative, but not limiting examples of boron compounds which may be used as ionic activating cocatalysts in this invention are tri-substituted ammonium salts such as:
decyldi(methyl)ammonium tetrakis(pentafluorophenyl) borate,
dodecyldi(methyl)ammonium tetrakis(pentafluorophenyl) borate,
tetradecyldi(methyl)ammonium tetrakis(pentafluorophenyl) borate,
hexaadecyldi(methyl)ammonium tetrakis(pentafluorophenyl) borate,
octadecyldi(methyl)ammonium tetrakis(pentafluorophenyl) borate,
eicosyldi(methyl)ammonium tetrakis(pentafluorophenyl) borate,
methyldi(decyl)ammonium tetrakis(pentafluorophenyl) borate,
methyldi(dodecyl)ammonium tetrakis(pentafluorophenyl) borate,
methyldi(tetradecyl)ammonium tetrakis(pentafluorophenyl) borate,
methyldi(hexadecyl)ammonium tetrakis(pentafluorophenyl) borate,
methyldi(octadecyl)ammonium tetrakis(pentafluorophenyl) borate,
methyldi(eicosyl)ammonium tetrakis(pentafluorophenyl) borate,
tridecylammonium tetrakis(pentafluorophenyl) borate,
tridodecylammonium tetrakis(pentafluorophenyl) borate,
tritetradecylammonium tetrakis(pentafluorophenyl) borate,
trihexadecylammonium tetrakis(pentafluorophenyl) borate,
trioctadecylammonium tetrakis(pentafluorophenyl) borate,
trieicosylammonium tetrakis(pentafluorophenyl) borate,
decyldi(n-butyl)ammonium tetrakis(pentafluorophenyl) borate,
dodecyldi(n-butyl)ammonium tetrakis(pentafluorophenyl) borate,
octadecyldi(n-butyl)ammonium tetrakis(pentafluorophenyl) borate,
N,N-didodecylanilinium tetrakis(pentafluorophenyl) borate,
N-methyl-N-dodecylanilinium tetrakis(pentafluorophenyl) borate,
N,N-di(octadecyl)(2,4,6-trimethylanilinium) tetrakis(pentafluorophenyl) borate,
cyclohexyldi(dodecyl)ammonium tetrakis(pentafluorophenyl)borate, and
methyldi(dodecyl)ammonium tetrakis-(2,3,4,6-tetrafluorophenyl) borate.

Suitable similarly substituted sulfonium or phosphonium salts such as,
di(decyl)sulfonium tetrakis(pentafluorophenyl) borate,
(n-butyl)dodecylsulfonium tetrakis(pentafluorophenyl) borate, tridecylphosphonium tetrakis(pentafluorophenyl) borate,
di(octadecyl)methylphosphonium tetrakis(pentafluorophenyl) borate, and
tri(tetradecyl)phosphonium tetrakis(pentafluorophenyl) borate, may also be named.

Preferred activators are di(octadecyl)methylammonium tetrakis(pentafluorophenyl)borate and di(octadecyl)(n-butyl)ammonium tetrakis(pentafluorophenyl)borate.

Suitable catalysts for use herein include any compound or complex of a metal of Groups 3–10 of the Periodic Table of the Elements capable of being activated to olefin insertion and polymerization by the present ammonium salt activators. Examples include Group 10 diimine derivatives corresponding to the formula:

M* is Ni(II) or Pd(II);
K is halo, hydrocarbyl, or hydrocarbyloxy;
Ar* is an aryl group, especially 2,6-diisopropylphenyl or aniline group;
CT—CT is 1,2-ethanediyl, 2,3-butanediyl, or form a fused ring system wherein the two T groups together are a 1,8-naphthanediyl group; and
$A^-$ is an inert noncoordinating anion.

The foregoing catalysts are disclosed by M. Brookhart, et al., in *J. Am. Chem. Soc.*, 118, 267–268(1996) and *J. Am. Chem. Soc.*, 117, 6414–6415(1995), as being active polymerization catalysts especially for polymerization of α-olefins, either alone or in combination with polar comomoners such as vinyl chloride, alkyl acrylates and alkyl methacrylates.

Additional catalysts include derivatives of Group 3, 4, or Lanthanide metals which are in the +2, +3, or +4 formal oxidation state. Preferred compounds include metal complexes containing from 1 to 3 π-bonded anionic or neutral ligand groups, which may be cyclic or non-cyclic delocalized π-bonded anionic ligand groups. Exemplary of such π-bonded anionic ligand groups are conjugated or nonconjugated, cyclic or non-cyclic dienyl groups, allyl groups, boratabenzene groups, and arene groups. By the term "π-bonded" is meant that the ligand group is bonded to the transition metal by a sharing of electrons from a partially delocalized π-bond.

Each atom in the delocalized π-bonded group may independently be substituted with a radical selected from the group consisting of hydrogen, halogen, hydrocarbyl, halohydrocarbyl, hydrocarbyl-substituted metalloid radicals wherein the metalloid is selected from Group 14 of the Periodic Table of the Elements, and such hydrocarbyl- or hydrocarbyl-substituted metalloid radicals further substituted with a Group 15 or 16 hetero atom containing moiety. Included within the term "hydrocarbyl" are $C_{1-20}$ straight, branched and cyclic alkyl radicals, $C_{6-20}$ aromatic radicals, $C_{7-20}$ alkyl-substituted aromatic radicals, and $C_{7-20}$ aryl-substituted alkyl radicals. In addition two or more such radicals may together form a fused ring system, including partially or fully hydrogenated fused ring systems, or they may form a metallocycle with the metal. Suitable hydrocarbyl-substituted organometalloid radicals include mono-, di- and tri-substituted organometalloid radicals of Group 14 elements wherein each of the hydrocarbyl groups contains from 1 to 20 carbon atoms. Examples of suitable hydrocarbyl-substituted organometalloid radicals include trimethylsilyl, triethylsilyl, ethyldimethylsilyl, methyldiethylsilyl, triphenylgermyl, and trimethylgermyl groups. Examples of Group 15 or 16 hetero atom containing moieties include amine, phosphine, ether or thioether moieties or divalent derivatives thereof, e. g. amide, phosphide, ether or thioether groups bonded to the transition metal or Lanthanide metal, and bonded to the hydrocarbyl group or to the hydrocarbyl-substituted metalloid containing group.

Examples of suitable anionic, delocalized π-bonded groups include cyclopentadienyl, indenyl, fluorenyl, tetrahydroindenyl, tetrahydrofluorenyl, octahydrofluorenyl, pentadienyl, cyclohexadienyl, dihydroanthracenyl, hexahydroanthracenyl, decahydroanthracenyl groups, and boratabenzene groups, as well as $C_{1-10}$ hydrocarbyl-substituted or $C_{1-10}$ hydrocarbyl-substituted silyl substituted derivatives thereof. Preferred anionic delocalized π-bonded groups are cyclopentadienyl, pentamethylcyclopentadienyl, tetramethylcyclopentadienyl, tetramethylsilylcyclopentadienyl, indenyl, 2,3-dimethylindenyl, fluorenyl, 2-methylindenyl, 2-methyl-4-phenylindenyl, tetrahydrofluorenyl, octahydrofluorenyl, and tetrahydroindenyl.

The boratabenzenes are anionic ligands which are boron containing analogues to benzene. They are previously known in the art having been described by G. Herberich, et al., in *Organometallics*, 14,1, 471–480 (1995). Preferred boratabenzenes correspond to the formula:

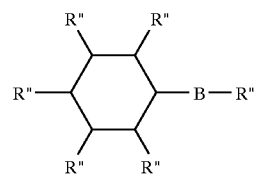

wherein R" is selected from the group consisting of hydrocarbyl, silyl, or germyl, said R" having up to 20 non-hydrogen atoms. In complexes involving divalent derivatives of such delocalized π-bonded groups one atom thereof is bonded by means of a covalent bond or a covalently bonded divalent group to another atom of the complex thereby forming a bridged system.

A suitable class of catalysts are transition metal complexes corresponding to the formula:

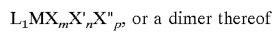

$L_1MX_mX'_nX''_p$, or a dimer thereof wherein:

L is an anionic, delocalized, π-bonded group that is bound to M, containing up to 50 non-hydrogen atoms, optionally two L groups may be joined together forming a bridged structure, and further optionally one L may be bound to X;

M is a metal of Group 4 of the Periodic Table of the Elements in the +2, +3 or +4 formal oxidation state;

X is an optional, divalent substituent of up to 50 non-hydrogen atoms that together with L forms a metallocycle with M;

X' is an optional neutral ligand having up to 20 non-hydrogen atoms;

X" each occurrence is a monovalent, anionic moiety having up to 40 non-hydrogen atoms, optionally, two X" groups may be covalently bound together forming a divalent dianionic moiety having both valences bound to M, or, optionally 2 X" groups may be covalently bound together to form a neutral, conjugated or nonconjugated diene that is π-bonded to M (whereupon M is in the +2 oxidation state), or further optionally one or more X" and one or more X' groups may be bonded together thereby forming a moiety that is both covalently bound to M and coordinated thereto by means of Lewis base functionality;

l is 0, 1 or 2;

m is 0 or 1;

n is a number from 0 to 3;

p is an integer from 0 to 3; and the sum, l+m+p, is equal to the formal oxidation state of M, except when 2 X" groups together form a neutral conjugated or non-conjugated diene that is π-bonded to M, in which case the sum l+m is equal to the formal oxidation state of M.

Preferred complexes include those containing either one or two L groups. The latter complexes include those containing a bridging group linking the two L groups. Preferred bridging groups are those corresponding to the formula $(ER^*_2)_x$ wherein E is silicon, germanium, tin, or carbon, R* independently each occurrence is hydrogen or a group selected from silyl, hydrocarbyl, hydrocarbyloxy and combinations thereof, said R* having up to 30 carbon or silicon atoms, and x is 1 to 8. Preferably, R* independently each occurrence is methyl, ethyl, propyl, benzyl, tert-butyl, phenyl, methoxy, ethoxy or phenoxy.

Examples of the complexes containing two L groups are compounds corresponding to the formula:

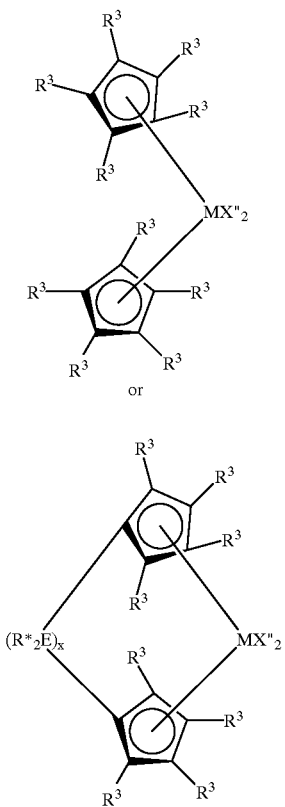

wherein:

M is zirconium, zirconium or hafnium, preferably zirconium or hafnium, in the +2 or +4 formal oxidation state;

$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative (that is, a hydrocarbadiyl, siladiyl or germadiyl group) thereby forming a fused ring system, and X" independently each occurrence is an anionic ligand group of up to 40 non-hydrogen atoms, or two X" groups together form a divalent anionic ligand group of up to 40 non-hydrogen atoms or together are a conjugated diene having from 4 to 30 non-hydrogen atoms forming a π-complex with M, whereupon M is in the +2 formal oxidation state, and R*, E and x are as previously defined.

The foregoing metal complexes are especially suited for the preparation of polymers having stereoregular molecular structure. In such capacity it is preferred that the complex possesses $C_s$ symmetry or possesses a chiral, stereorigid structure. Examples of the first type are compounds possessing different delocalized π-bonded systems, such as one cyclopentadienyl group and one fluorenyl group. Similar systems based on Ti(IV) or Zr(IV) were disclosed for preparation of syndiotactic olefin polymers in Ewen, et al., *J. Am. Chem. Soc.* 110, 6255–6256 (1980). Examples of chiral structures include rac bis-indenyl complexes. Similar systems based on Ti(IV) or Zr(IV) were disclosed for preparation of isotactic olefin polymers in Wild et al., *J. Organomet. Chem.*, 232, 233–47, (1982).

Exemplary bridged ligands containing two π-bonded groups are: (dimethylsilyl-bis(cyclopentadienyl)), (dimethylsilyl-bis(methylcyclopentadienyl)), (dimethylsilyl-bis(ethylcyclopentadienyl)), (dimethylsilyl-bis(t-butylcyclopentadienyl)), (dimethylsilyl-bis(tetramethylcyclopentadienyl)), (dimethylsilyl-bis(indenyl)), (dimethylsilyl-bis(tetrahydroindenyl)), (dimethylsilyl-bis(fluorenyl)), (dimethylsilyl-bis(tetrahydrofluorenyl)), (dimethylsilyl-bis(2-methyl-4-phenylindenyl)), (dimethylsilyl-bis(2-methylindenyl)), (dimethylsilyl-cyclopentadienyl-fluorenyl), (dimethylsilyl-cyclopentadienyl-octahydrofluorenyl), (dimethylsilyl-cyclopentadienyl-tetrahydrofluorenyl), (1, 1, 2, 2-tetramethyl-1, 2-disilyl-bis-cyclopentadienyl), (1, 2-bis(cyclopentadienyl)ethane, and (isopropylidene-cyclopentadienyl-fluorenyl).

Preferred X" groups are selected from hydride, hydrocarbyl, silyl, germyl, halohydrocarbyl, halosilyl, silylhydrocarbyl and aminohydrocarbyl groups, or two X" groups together form a divalent derivative of a conjugated diene or else together they form a neutral, π-bonded, conjugated diene. Most preferred X" groups are $C_{1-20}$ hydrocarbyl groups.

A further class of metal complexes utilized in the present invention corresponds to the preceding formula $L_lMX_mX'_nX''_p$, or a dimer thereof, wherein X is a divalent substituent of up to 50 non-hydrogen atoms that together with L forms a metallocycle with M.

Preferred divalent X substituents include groups containing up to 30 non-hydrogen atoms comprising at least one atom that is oxygen, sulfur, boron or a member of Group 14 of the Periodic Table of the Elements directly attached to the delocalized π-bonded group, and a different atom, selected from the group consisting of nitrogen, phosphorus, oxygen or sulfur that is covalently bonded to M.

A preferred class of such Group 4 metal coordination complexes used according to the present invention corresponds to the formula:

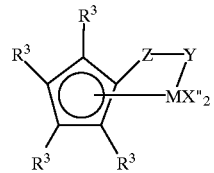

wherein:

M is titanium or zirconium, preferably titanium in the +2, +3, or +4 formal oxidation state;

$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative (that is, a hydrocarbadiyl, siladiyl or germadiyl group) thereby forming a fused ring system, each X" is a halo, hydrocarbyl, hydrocarbyloxy or silyl group, said group having up to 20 non-hydrogen atoms, or two X" groups together form a neutral $C_{5-30}$ conjugated diene or a divalent derivative thereof;

Y is —O—, —S—, —NR*—, —PR*—; and

Z is $SiR*_2$, $CR*_2$, $SiR*_2SiR*_2$, $CR*_2CR*_2$, CR*=CR*, $CR*_2SiR*_2$, or $GeR*_2$, wherein R* is as previously defined.

Illustrative Group 4 metal complexes that may be employed in the practice of the present invention include: cyclopentadienyltitaniumtrimethyl, cyclopentadienyltitaniumtriethyl, cyclopentadienyltitaniumtriisopropyl, cyclopentadienyltitaniumtriphenyl, cyclopentadienyltitaniumtribenzyl,
cyclopentadienyltitanium-2,4-dimethylpentadienyl,
cyclopentadienyltitanium-2,4-dimethylpentadienyl•triethylphosphine,
cyclopentadienyltitanium-2,4-dimethylpentadienyl•trimethylphosphine,
cyclopentadienyltitaniumdimethylmethoxide,
cyclopentadienyltitaniumdimethylchloride,
pentamethylcyclopentadienyltitaniumtrimethyl,
indenyltitaniumtrimethyl,
indenyltitaniumtriethyl,
indenyltitaniumtripropyl,
indenyltitaniumtriphenyl,
tetrahydroindenyltitaniumtribenzyl,
pentamethylcyclopentadienyltitaniumtriisopropyl,
pentamethylcyclopentadienyltitaniumtribenzyl,
pentamethylcyclopentadienyltitaniumdimethylmethoxide,
pentamethylcyclopentadienyltitaniumdimethylchloride,
bis($\eta^5$-2,4-dimethylpentadienyl)titanium,
bis($\eta^5$-2,4-dimethylpentadienyl)titanium•trimethylphosphine,
bis($\eta^5$-2,4-dimethylpentadienyl)titanium•triethylphosphine,
octahydrofluorenyltitaniumtrimethyl,
tetrahydroindenyltitaniumtrimethyl,
tetrahydrofluorenyltitaniumtrimethyl,
(tert-butylamido)(1,1-dimethyl-2,3,4,9,10-$\eta$-1,4,5,6,7,8-hexahydronaphthalenyl)dimethylsilanetitaniumdimethyl,
(tert-butylamido)(1,1,2,3-tetramethyl-2,3,4,9,10-$\eta$-1,4,5,6,7,8-hexahydronaphthalenyl)dimethylsilanetitaniumdimethyl,
(tert-butylamido)(tetramethyl-$\eta^5$-cyclopentadienyl) dimethylsilanetitanium dibenzyl,
(tert-butylamido)(tetramethyl-$\eta^5$-cyclopentadienyl) dimethylsilanetitanium dimethyl,
(tert-butylamido)(tetramethyl-$\eta^5$-cyclopentadienyl)-1,2-ethanediyltitanium dimethyl,
(tert-butylamido)(tetramethyl-$\eta^5$-indenyl) dimethylsilanetitanium dimethyl,
(tert-butylamido)(tetramethyl-$\eta^5$-cyclopentadienyl) dimethylsilane titanium (III) 2-(dimethylamino)benzyl;
(tert-butylamido)(tetramethyl-$\eta^5$-cyclopentadienyl) dimethylsilanetitanium (III) allyl,
(tert-butylamido)(tetramethyl-$\eta^5$-cyclopentadienyl) dimethylsilanetitanium (III) 2,4-dimethylpentadienyl,
(tert-butylamido)(tetramethyl-$\eta^5$-cyclopentadienyl) dimethylsilanetitanium (II) 1,4-diphenyl-1,3-butadiene,
(tert-butylamido)(tetramethyl-$\eta^5$-cyclopentadienyl) dimethylsilanetitanium (II) 1,3-pentadiene,
(tert-butylamido)(2-methylindenyl)dimethylsilanetitanium (II) 1,4-diphenyl-1,3-butadiene,
(tert-butylamido)(2-methylindenyl)dimethylsilanetitanium (II) 2,4-hexadiene,
(tert-butylamido)(2-methylindenyl)dimethylsilanetitanium (IV) 2,3-dimethyl-1,3-butadiene,
(tert-butylamido)(2-methylindenyl)dimethylsilanetitanium (IV) isoprene,
(tert-butylamido)(2-methylindenyl)dimethylsilanetitanium (IV) 1,3-butadiene,
(tert-butylamido)(2,3-dimethylindenyl) dimethylsilanetitanium (IV) 2,3-dimethyl-1,3-butadiene,
(tert-butylamido)(2,3-dimethylindenyl) dimethylsilanetitanium (IV) isoprene
(tert-butylamido)(2,3-dimethylindenyl) dimethylsilanetitanium (IV) dimethyl
(tert-butylamido)(2,3-dimethylindenyl) dimethylsilanetitanium (IV) dibenzyl
(tert-butylamido)(2,3-dimethylindenyl) dimethylsilanetitanium (IV) 1,3-butadiene,
(tert-butylamido)(2,3-dimethylindenyl) dimethylsilanetitanium (II) 1,3-pentadiene,
(tert-butylamido)(2,3-dimethylindenyl) dimethylsilanetitanium (II) 1,4-diphenyl-1,3-butadiene,
(tert-butylamido)(2-methylindenyl)dimethylsilanetitanium (II) 1,3-pentadiene,
(tert-butylamido)(2-methylindenyl)dimethylsilanetitanium (IV) dimethyl,
(tert-butylamido)(2-methylindenyl)dimethylsilanetitanium (IV) dibenzyl,
(tert-butylamido)(2-methyl-4-phenylindenyl) dimethylsilanetitanium (II) 1,4-diphenyl-1,3-butadiene,
(tert-butylamido)(2-methyl-4-phenylindenyl) dimethylsilanetitanium (II) 1,3-pentadiene,
(tert-butylamido)(2-methyl-4-phenylindenyl) dimethylsilanetitanium (II) 2,4-hexadiene,
(tert-butylamido)(tetramethyl-$\eta^5$-cyclopentadienyl) dimethyl-silanetitanium (IV) 1,3-butadiene,
(tert-butylamido)(tetramethyl-$\eta^5$-cyclopentadienyl) dimethylsilanetitanium (IV) 2,3-dimethyl-1,3-butadiene,
(tert-butylamido)(tetramethyl-$\eta^5$-cyclopentadienyl) dimethylsilanetitanium (IV) isoprene,
(tert-butylamido)(tetramethyl-$\eta^5$-cyclopentadienyl) dimethyl-silanetitanium (II) 1,4-dibenzyl-1,3-butadiene,
(tert-butylamido)(tetramethyl-$\eta^5$-cyclopentadienyl) dimethylsilanetitanium (II) 2,4-hexadiene,
(tert-butylamido)(tetramethyl-$\eta^5$-cyclopentadienyl) dimethyl-silanetitanium (II) 3-methyl-1,3-pentadiene,
(tert-butylamido)(2,4-dimethylpentadien-3-yl) dimethylsilanetitaniumdimethyl,
(tert-butylamido)(6,6-dimethylcyclohexadienyl) dimethylsilanetitaniumdimethyl,
(tert-butylamido)(1,1-dimethyl-2,3,4,9,10-$\eta$-1,4,5,6,7,8-hexahydronaphthalen-4-yl) dimethylsilanetitaniumdimethyl,
(tert-butylamido)(1,1,2,3-tetramethyl-2,3,4,9,10-$\eta$-1,4,5,6,7,8-hexahydronaphthalen-4-yl) dimethylsilanetitaniumdimethyl
(tert-butylamido)(tetramethyl-$\eta^5$-cyclopentadienyl methylphenylsilanetitanium (IV) dimethyl,
(tert-butylamido)(tetramethyl-$\eta^5$-cyclopentadienyl methylphenylsilanetitanium (II) 1,4-diphenyl-1,3-butadiene,
1-(tert-butylamido)-2-(tetramethyl-$\eta^5$-cyclopentadienyl) ethanediyltitanium (IV) dimethyl, and
1-(tert-butylamido)-2-(tetramethyl-$\eta^5$-cyclopentadienyl) ethanediyl-titanium (II) 1,4-diphenyl-1,3-butadiene.

Complexes containing two L groups including bridged complexes suitable for use in the present invention include:
bis(cyclopentadienyl)zirconiumdimethyl,
bis(cyclopentadienyl)zirconium dibenzyl,
bis(cyclopentadienyl)zirconium methyl benzyl,
bis(cyclopentadienyl)zirconium methyl phenyl,
bis(cyclopentadienyl)zirconiumdiphenyl,
bis(cyclopentadienyl)titanium-allyl,
bis(cyclopentadienyl)zirconiummethylmethoxide,
bis(cyclopentadienyl)zirconiummethylchloride,
bis(pentamethylcyclopentadienyl)zirconiumdimethyl,
bis(pentamethylcyclopentadienyl)titaniumdimethyl,
bis(indenyl)zirconiumdimethyl,
indenylfluorenylzirconiumdimethyl,
bis(indenyl)zirconiummethyl(2-(dimethylamino)benzyl),
bis(indenyl)zirconium methyltrimethylsilyl,
bis(tetrahydroindenyl)zirconium methyltrimethylsilyl,
bis(pentamethylcyclopentadienyl)zirconiummethylbenzyl,
bis(pentamethylcyclopentadienyl)zirconiumdibenzyl,
bis(pentamethylcyclopentadienyl)zirconiummethylmethoxide, bis(pentamethylcyclopentadienyl)zirconiummethylchloride,
bis(methylethylcyclopentadienyl)zirconiumdimethyl,
bis(butylcyclopentadienyl)zirconium dibenzyl,
bis(t-butylcyclopentadienyl)zirconiumdimethyl,
bis(ethyltetramethylcyclopentadienyl)zirconiumdimethyl,
bis(methylpropylcyclopentadienyl)zirconium dibenzyl,
bis(trimethylsilylcyclopentadienyl)zirconium dibenzyl,
dimethylsilyl-bis(cyclopentadienyl)zirconiumdimethyl,
dimethylsilyl-bis(tetramethylcyclopentadienyl)titanium-(III) allyl
dimethylsilyl-bis(t-butylcyclopentadienyl) zirconiumdichloride,
dimethylsilyl-bis(n-butylcyclopentadienyl) zirconiumdichloride,
(methylene-bis(tetramethylcyclopentadienyl)titanium(III) 2-(dimethylamino)benzyl,
(methylene-bis(n-butylcyclopentadienyl)titanium(III) 2-(dimethylamino)benzyl,
dimethylsilyl-bis(indenyl)zirconiumbenzylchloride,
dimethylsilyl-bis(2-methylindenyl)zirconiumdimethyl,
dimethylsilyl-bis(2-methyl-4-phenylindenyl) zirconiumdimethyl,
dimethylsilyl-bis(2-methylindenyl)zirconium-1,4-diphenyl-1,3-butadiene,
dimethylsilyl-bis(2-methyl-4-phenylindenyl)zirconium (II) 1,4-diphenyl-1,3-butadiene,
dimethylsilyl-bis(tetrahydroindenyl)zirconium(II) 1,4-diphenyl-1,3-butadiene,
dimethylsilyl-bis(fluorenyl)zirconiummethylchloride,
dimethylsilyl-bis(tetrahydrofluorenyl)zirconium bis (trimethylsilyl),
(isopropylidene)(cyclopentadienyl)(fluorenyl) zirconiumdibenzyl, and
dimethylsilyl(tetramethylcyclopentadienyl)(fluorenyl) zirconium dimethyl.

Other catalysts, especially catalysts containing other Group 4 metals, will, of course, be apparent to those skilled in the art.

The cocatalysts of the invention may also be used in combination with a tri(hydrocarbyl)aluminum compound having from 1 to 10 carbons in each hydrocarbyl group, an oligomeric or polymeric alumoxane compound, a di(hydrocarbyl)(hydrocarbyloxy)aluminum compound having from 1 to 20 carbons in each hydrocarbyl or hydrocarbyloxy group, or a mixture of the foregoing compounds, if desired. These aluminum compounds are usefully employed for their beneficial ability to scavenge impurities such as oxygen, water, and aldehydes from the polymerization mixture.

Suitable di(hydrocarbyl)(hydrocarbyloxy)aluminum compounds correspond to the formula $T^1{}_2AlOT^2$ wherein $T^1$ is $C_{3-6}$ secondary or tertiary alkyl, most preferably isopropyl, isobutyl or tert-butyl; and $T^2$ is a $C_{12-30}$ alkaryl radical or aralkyl radical, most preferably, 2,6-di(t-butyl)-4-methylphenyl, 2,6-di(t-butyl)-4-methyltolyl, 2,6-di(i-butyl)-4-methylphenyl, or 4-(3',5'-ditertiarybutyltolyl)-2,6-ditertiarybutylphenyl.

Preferred aluminum compounds include $C_{2-6}$ trialkyl aluminum compounds, especially those wherein the alkyl groups are ethyl, propyl, isopropyl, n-butyl, isobutyl, pentyl, neopentyl, or isopentyl, dialkyl(aryloxy)aluminum compounds containing from 1–6 carbons in the alkyl group and from 6 to 18 carbons in the aryl group (especially (3,5-di (t-butyl)- 4-methylphenoxy)diisobutylaluminum), methylalumoxane, modified methylalumoxane and diisobutylalumoxane. The molar ratio of aluminum compound to metal complex is preferably from 1:10,000 to 1000:1, more preferably from 1:5000 to 100:1, most preferably from 1:100 to 100:1.

The molar ratio of catalyst/cocatalyst employed preferably ranges from 1:10 to 10:1, more preferably from 1:5 to 1:1, most preferably from 1:1.5 to 1:1. Mixtures of the activating cocatalysts of the present invention may also be employed if desired.

Suitable addition polymerizable monomers include ethylenically unsaturated monomers, acetylenic compounds, conjugated or non-conjugated dienes, and polyenes. Preferred monomers include olefins, for examples alpha-olefins having from 2 to 20,000, preferably from 2 to 20, more preferably from 2 to 8 carbon atoms and combinations of two or more of such alpha-olefins. Particularly suitable alpha-olefins include, for example, ethylene, propylene, 1-butene, 1-pentene, 4-methylpentene-1, 1-hexene, 1-heptene, 1-octene, 1-nonene, 1-decene, 1-undecene, 1-dodecene, 1-tridecene, 1-tetradecene, 1-pentadecene, or combinations thereof, as well as long chain vinyl terminated oligomeric or polymeric reaction products formed during the polymerization, and $C_{10-30}$ α-olefins specifically added to the reaction mixture in order to produce relatively long chain branches in the resulting polymers. Preferably, the alpha-olefins are ethylene, propene, 1-butene, 4-methyl-pentene-1, 1-hexene, 1-octene, and combinations of ethylene and/or propene with one or more of such other alpha-olefins. Other preferred monomers include styrene, halo- or alkyl substituted styrenes, tetrafluoroethylene, vinylcyclobutene, 1,4-hexadiene, dicyclopentadiene, ethylidene norbornene, and 1,7-octadiene. Mixtures of the above-mentioned monomers may also be employed.

In general, the polymerization may be accomplished at conditions well known in the prior art for Ziegler-Natta or Kaminsky-Sinn type polymerization reactions. Suspension, solution, slurry, gas phase or high pressure, whether employed in batch or continuous form or other process conditions, may be employed if desired. Examples of such well known polymerization processes are depicted in WO 88/02009, U.S. Pat. Nos. 5,084,534, 5,405,922, 4,588,790, 5,032,652, 4,543,399, 4,564,647, 4,522,987, and elsewhere. Preferred polymerization temperatures are from 0–250° C. Preferred polymerization pressures are from atmospheric to 3000 atmospheres.

However, the advantages of the invention are particularly noticed when the present catalyst system is used in a solution polymerization, more preferably a continuous solution polymerization process, in the presence of an aliphatic or alicyclic liquid diluent. By the term "continuous polymerization" is meant that at least the products of the polymerization are continuously removed from the reaction mixture, such as for example by devolatilization of a portion of the reaction mixture. Preferably one or more reactants are also continuously added to the polymerization mixture during the polymerization. Examples of suitable aliphatic or alicyclic liquid diluents include straight and branched-chain hydrocarbons such as isobutane, butane, pentane, hexane, heptane, octane, and mixtures thereof; alicyclic hydrocarbons such as cyclohexane, cycloheptane, methylcyclohexane, methylcycloheptane, and mixtures thereof; and perfluorinated hydrocarbons such as perfluorinated $C_{4-10}$ alkanes, and the like. Suitable diluents also include aromatic hydrocarbons (particularly for use with aromatic α-olefins such as styrene or ring alkyl-substituted styrenes) including toluene, ethylbenzene or xylene, as well as liquid olefins (which may act as monomers or comonomers) including ethylene, propylene, butadiene, cyclopentene, 1-hexene, 3-methyl-1-pentene, 4-methyl-1-pentene, 1,4-hexadiene, 1-octene, 1-decene, styrene, divinylbenzene, allylbenzene, vinyltoluene (including all isomers alone or in admixture), and the like. Mixtures of the foregoing are also suitable.

In most polymerization reactions the molar ratio of catalyst:polymerizable compounds employed is from $10^{-12}$:1 to $10^{-1}$:1, more preferably from $10^{-12}$:1 to $10^{-5}$:1.

The catalyst system of the invention may also be utilized in combination with at least one additional homogeneous or heterogeneous polymerization catalyst in separate reactors connected in series or in parallel to prepare polymer blends having desirable properties. An example of such a process is disclosed in WO 94/00500, equivalent to U.S. Ser. No. 07/904,770. A more specific process is disclosed in copending application U.S. Ser. No. 08/10958, filed Jan. 29, 1993. The teachings of the foregoing publications and pending applications are hereby incorporated by reference.

Molecular weight control agents can be used in combination with the present cocatalysts. Examples of such molecular weight control agents include hydrogen, trialkyl aluminum compounds or other known chain transfer agents. A particular benefit of the use of the present cocatalysts is the ability (depending on reaction conditions) to produce narrow molecular weight distribution a-olefin homopolymers and copolymers in greatly improved catalyst efficiencies. Preferred polymers have Mw/Mn of less than 2.5, more preferably less than 2.3. Such narrow molecular weight distribution polymer products are highly desirable due to improved tensile strength properties.

It is understood that the present invention is operable in the absence of any component which has not been specifically disclosed. The following examples are provided in order to further illustrate the invention and are not to be construed as limiting. Unless stated to the contrary, all parts and percentages are expressed on a weight basis.

EXAMPLE 1

Preparation of di(octadecyl)methylammonium tetrakis(pentafluoro-phenyl)borate (($C_{18}H_{37}$)$_2$N(Me)H$^+$B($C_6F_5$)$_4$$^-$)

di(octadecyl)methylammonium chloride (($C_{18}H_{37}$)$_2$NMeH$^+$Cl$^-$)

0.50 g of dioctydecylmethylamine (($C_{18}H_{37}$)$_2$N(Me)) (Aldrich Chemical) was dissolved in ~50 mL of hexane. HCl in Et$_2$O (1M, Aldrich, 1.17 mL) was added by syringe, resulting in the immediate formation of a white precipitate. The mixture was stirred for several hours, then filtered through a medium porosity (10–15 μm) frit. The solid that remained on the frit was washed with additional hexane, then dried on the frit and finally under vacuum. Approximately 0.56 g of product as a white solid was obtained.

Preparation A)

In the drybox, 0.50 g of LiB($C_6F_5$)$_4$ and 0.38 g of ($C_{18}H_{37}$)$_2$N(Me)H$^+$Cl$^-$ were mixed as solids in a small jar. The jar was removed from the drybox and 30 mL of distilled water was added. The LiB($C_6F_5$)$_4$ appeared to dissolve, but the amine hydrochloride floated on top of the liquid. The mixture was placed on a mechanical shaker for one hour. During this time, the amine hydrochloride slowly disappeared and was replaced by a sticky white precipitate which adhered to the walls of the jar. At the end of one hour, 20 mL of toluene was added and the mixture placed on the shaker again for 10 minutes. The mixture was then poured into a separatory funnel and 20 mL of saturated aqueous sodium carbonate was added. The layers were separated and the aqueous layer discarded. The organic layer was washed with 20 mL of H$_2$O, dried over MgSO$_4$, and filtered into a small Schlenk tube. The volatile materials were then removed under vacuum to leave a pale brown viscous oil. The Schlenk tube was taken into the drybox, and the oil dissolved in cyclohexane. This solution was made up to 10 mL using a volumetric flask. By weighing the Schlenk tube before and after removal of the product with cyclohexane, the product weight was determined to be 0.80 g. Assuming a molecular weight of 1216.08 g/mol for ($C_{18}H_{37}$)$_2$N(Me)H$^+$B($C_6F_5$)$_4$$^-$ the solution concentration is calculated to be 0.066 M, 10.3 weight percent.

Preparation B)

In the drybox, 0.50 g of LiB($C_6F_5$)$_4$ and 0.42 g of ($C_{18}H_{37}$)$_2$N(Me)H$^+$Cl$^-$ were slurried in 25 mL of toluene in a small bottle. The bottle was removed from the drybox and 20 mL of distilled water was added. The bottle was placed on a shaker and agitated thoroughly for one hour. At the end of this time, 20 mL of saturated aqueous sodium carbonate was added and the mixture transferred to a separatory funnel. The layers were separated and the aqueous layer discarded. The organic layer was washed with 20 mL of saturated Na$_2$CO$_3$ followed by 20 mL of H$_2$O, dried over MgSO$_4$, and filtered. The volatile materials were then removed under vacuum to leave 0.71 g of a pale brown oil. The flask was taken into the drybox, and the oil was dissolved in 10 mL of mixed alkanes (Isopar™ E, available from Exxon Chemicals Inc.) to give a solution concentration of 0.0075 M, 9.0 weight percent, which was then further diluted to give a final solution concentration of 0.0075 M.

Preparation C)

In the drybox, 0.50 g of LiB($C_6F_5$)$_4$ and 0.42 g of (Cl8H$_{37}$)$_2$N(Me)H$^+$Cl$^-$ were slurried in 20 mL of cyclohexane. The mixture was heated to reflux for 1.5 hours. Shortly after heating began, the solution became clear. At the end of the reflux time, the mixture was cooled to room temperature and filtered through a medium porosity (10–15 mm) fritted funnel using diatomaceous earth filter aid (Celite™). The solution was transferred into a four ounce bottle and removed from the drybox, sparged briefly with nitrogen, then returned to the drybox. An aliquot was removed and the concentration measured by gravimetric analysis; a value of 0.022 M, 3.4 weight percent, was obtained for the solution concentration.

Polymerizations

A one gallon stirred reactor was charged with Isopar™ E solvent, 1-octene, and 5 mMol of hydrogen. The reactor was heated to 130° C. and saturated with ethylene to 450 psig (3.1 MPa). The catalyst composition was prepared in a drybox by syringing together 2.5 mMol of (t-butylamido) dimethyl($\eta^5$-tetramethylcyclopentadienyl)titanium ($\eta^4$-1,3-pentadiene) catalyst, di(octadecyl)methylammonium tetrakis(penta-fluorophenyl)borate cocatalyst (prepared by one of the foregoing preparations A), B) or C), and optionally a third component (triisobutylaluminum modified methylalumoxane (MMAO), trisiobutylaluminum (TIBA), or (2,6-di(t-butyl)-4-methylphenoxy)di(i-butyl)aluminum (DIBAL-BOT)). This mixture was then transferred by syringe to an addition loop and injected into the reactor over approximately 4 minutes. The polymerization was allowed to proceed for 10 minutes while feeding ethylene on demand to maintain a pressure of 450 psig. (3.1 MPa). The polymer solution was either transferred from the reactor into a glass kettle followed by thorough drying using a vacuum oven or discarded. In cases where the polymer was isolated and dried, the catalyst efficiency was calculated as kilograms polymer per gram titanium. In cases where the polymer was not saved, the efficiency was calculated as kilograms ethylene consumed during the reaction per gram of titanium. Details of the polymerizations are shown in Table 1.

TABLE 1

| Run | Cocatalyst | (μmol) | 3rd Component | (μmol) | solvent (g) | Octene (g) | Eff. (Kg C$_2$H$_4$/gTi) |
|-----|------------|--------|---------------|--------|-------------|------------|---------------------------|
| 1   | A          | 2.5    | MMAO          | 25     | 1426        | 138        | 0.8                       |
| 2   | A          | 3.75   | "             | "      | 1423        | 132        | 1.0                       |
| 3   | A          | 3.15   | "             | "      | 1415        | 138        | 0.9                       |
| 4   | A          | 5.0    | "             | "      | 1410        | 136        | 1.0                       |
| 5   | A          | 1.5    | "             | "      | 1433        | 137        | 0.5                       |
| 6   | A          | 3.75   | none          | 0      | 1432        | 130        | 0.5                       |
| 7   | A          | "      | MMAO          | 25     | 1462        | 137        | 0.6                       |
| 8   | A          | "      | TIBA          | "      | 1459        | 133        | 0.7                       |
| 9   | A          | "      | DIBAL-BOT     | "      | 1470        | 130        | 0.9                       |
| 10  | B          | "      | "             | 50     | 1427        | 139        | 1.5                       |
| 11  | C          | "      | "             | "      | 1420        | 140        | 0.9                       |

EXAMPLE 2

Preparation of bis(hydrogenated-tallowalkyl) methylammonium tetrakis(pentafluorophenyl)borate $((C_{18-22}H_{37-45})_2N^+(Me)HB^-(C_6F_5)_4)$ The synthetic steps of example 1, preparation C were substantially repeated excepting that the ammonium salt was prepared from the bis(hydrogenated-tallowalkyl) methylamine (a trialkyl amine containing a mixture of $C_{18-22}$ alkyl groups derived from tallow, available from Witco Corporation or Akzo Nobel).

Preparation A

Bis(hydrogenated-tallowalkyl)methylamine (KEMAMINE® T-9701 obtained from Witco Corporation; the molecular weight of this amine was calculated to be 513.8 from the "Total Amine Value" reported by the supplier) (5.65 g, 11.0 mmol) was dissolved in 50 mL of hexane. HCl in ether (1 M, 13.75 mL) was added by syringe, resulting in a white precipitate. The mixture was stirred for 30 minutes, then filtered using a glass frit having a pore size of 10-5 μm. The solid that remained was washed with hexane and dried under vacuum.

In the drybox, 1.20 g of the amine HCl salt obtained above (2.18 mmol) and 1.57 g of LiB(C$_6$F$_5$)$_4$ (2.29 mmol) were mixed in hexane and stirred for 2 hours at 25° C. At the end of this time, cyclohexane was added (10–15 mL) and the solution was filtered using a glass frit having a pore size of 10–15 μm and topped with a diatomaceous earth filter aid (Celite™). The concentration of this solution was measured gravimetrically to be 6.3 wt percent.

Preparation B

Bis(hydrogenated-tallowalkyl)methylamine (ARMEEN® M2HT obtained from Akzo Nobel; the molecular weight of this amine was reported on the certificate of analysis provided by the supplier to be 521.1) (5.00 g, 9.6 mmol) was dissolved in 50 mL of hexane. HCl in ether (1 M, 10.1 mL) was added by syringe, resulting in a white precipitate. The mixture was swirled by hand for 10 minutes, then filtered using a glass frit having a pore size of 10–15 μm. The white solid that remained was washed with hexane and dried under vacuum.

In the drybox, 2.00 g of the amine HCl salt obtained above (3.59 mmol) and 2.58 g of LiB(C$_6$F$_5$)$_4$ (3.77 mmol) were mixed as solids. Cyclohexane (30 mL) was added and the mixture was stirred for 2 hours. At the end of this time, the mixture was filtered using a glass frit having a pore size of 10–15 μm topped with Celite™ filter aid) to give a clear, pale brown solution. The concentration of this solution was measured gravimetrically to be 10.3 wt percent.

Preparation C (in situ generation of hydrochloride salt)

Bis(hydrogenated-tallowalkyl)methylamine (ARMEEN® M2HT, 1.0 g, 1.92 mmol) was dissolved in 25 mL of methylcyclohexane. Aqueous HCl (1 M, 1.92 mL) was added by syringe. The mixture was stirred for 30 minutes, then a solution of LiB(C$_6$F$_5$)$_4$ (1.32 g, 1.92 mmol) dissolved in 20 mL of water was added. The mixture was stirred for another 30 minutes. It was then poured into a separatory funnel and 50 mL of saturated aqueous NaCl was added. The layers were separated and the aqueous layer discarded. The organic layer was dried over MgSO$_4$ overnight. The mixture was then filtered using a glass frit having a pore size of 10–15 μm to give a clear pale brown solution. The solution was transferred to a bottle, sparged thoroughly with nitrogen, and taken into the drybox. The concentration of this solution was measured gravimetrically to be 17.5 wt percent.

Preparation D: Large scale

Methylcyclohexane (1200 mL) was placed in a 2 L cylindrical flask. While stirring, bis(hydrogenated-tallowalkyl)methylamine (ARMEEN® M2HT, 104 g, ground to a granular form) was added to the flask and stirred until completely dissolved. Aqueous HCl (1M, 200 mL) was added to the flask, and the mixture was stirred for 30 minutes. A white precipitate formed immediately. At the end of this time, LiB(C$_6$F$_5$)$_4$•Et$_2$O•3 LiCl (MW=887.3; 177.4 g) was added to the flask. The solution began to turn milky white. The flask was equipped with a 6" Vigreux column topped with a distillation apparatus and the mixture was heated (140° C. external wall temperature). A mixture of ether and methylcyclohexane was distilled from the flask. The two-phase solution was now only slightly hazy. The mixture was allowed to cool to room temperature, and the contents were placed in a 4 L separatory funnel. The aqueous layer was removed and discarded, and the organic layer was washed twice with H$_2$O and the aqueous layers again discarded. The product solution was divided into two equal portions for the evaluation of two workup procedures. These H$_2$O saturated methylcyclohexane solutions were measured to contain 0.48 wt percent diethylether (Et$_2$O).

Workup Procedure b 13× Molecular Sieve Technique

The solution (600 mL) was transferred into a 1 L flask, sparged thoroughly with nitrogen, and transferred into the drybox. The solution was passed through a column (1" diameter, 6" height) containing 13× molecular sieves. This reduced the level of Et$_2$O from 0.48 wt percent to 0.28 wt percent. The material was then stirred over fresh 13× sieves (20 g) for four hours. The Et$_2$O level was then measured to be 0.19 wt percent. The mixture was then stirred overnight, resulting in a further reduction in Et$_2$O level to approximately 40 ppm. The mixture was filtered using a funnel equipped with a glass frit having a pore size of 10–15 μm to give a clear solution (the molecular sieves were rinsed with additional dry methylcyclohexane). The concentration was measured by gravimetric analysis yielding a value of 16.7 wt percent.

Workup Procedure b Vacuum Technique

The solution (600 mL) was transferred to a 1 L flask and 35 g MgSO$_4$ was added. The mixture was stirred for 5 minutes, then filtered through a funnel equipped with a glass frit having a pore size of 10–15 μm into a second 1 L flask. The clear solution was sparged thoroughly with N$_2$, and transferred into the drybox. The volatile materials were removed under vacuum to leave a clear, pale yellow oil. This oil was redissolved in dry, deoxygenated methylcyclohexane and the concentration was measured by gravimetric analysis (23.5 wt percent). Analysis by GC indicated that the solution contained <20 ppm Et$_2$O.

Polymerization

The polymerization conditions of Example 1 were substantially repeated using the above tallow amine salt derivatives as activators and various transition metal complexes as catalysts. Results are contained in Table 2.

TABLE 2

| Run | Catalyst (mmol) | Cocat Prep (mmol) | 3rd Component (mmol) | Solvent (g) | Octene (g) | Efficiency (Kg C$_2$H$_4$/gTi) |
|---|---|---|---|---|---|---|
| 12 | A (1.5) | A (2.25) | DIBAL-BOT (15) | 1461 | 135 | 1.35 |
| 13 | A (1.5) | B (2.25) | DIBAL-BOT (15) | 1461 | 137 | 1.35 |
| 14 | A (1.5) | C (2.25) | DIBAL-BOT (15) | 1453 | 139 | 1.90 |
| 15 | B (0.5) | C (0.75) | DIBAL-BOT (5) | 1444 | 137 | 3.29 |
| 16 | A (0.5) | C (0.75) | DIBAL-BOT (5) | 1462 | 140 | 4.02 |
| 17 | B (0.5) | C (0.75) | DIBAL-BOT (5) | 1456 | 137 | 2.51 |
| 18 | C (0.5) | C (0.75) | DIBAL-BOT (5) | 1450 | 138 | 2.77 |

*A = (t-butylamido)dimethyl(h$^5$-tetramethylcyclopentadienyl)titanium (h$^4$-1,3-pentadiene)
B = (isopropylamido)(dimethyl)(h$^5$-2,3,4,6-tetramethylindenyl)titanium dimethyl
C = (t-butylamido)(dimethyl)(h$^5$-2,3,4,6-tetramethylindenyl)titanium dimethyl

EXAMPLE 3

Preparation of di(hydrogenated tallowalkyl) methylammonium methyltris(pentafluorophenyl) phenylborate (($C_{18-22}H_{37-45}$)$_2$N(Me)H$^+$B($C_6H_5$)($C_6F_5$)$_3^-$)

The synthetic steps of example 2 were substantially repeated excepting that the borate salt was the lithium salt of methyltris(pentafluorophenyl)borate.

Polymerizations

A one gallon stirred reactor was charged with 1440 mL Isopar™ E solvent, 126 g of 1-octene, and hydrogen (about 25 ml at 35 Δpsi, 0.24 ΔMPa). The reactor was heated to 130° C. and saturated with ethylene to 450 psig (3.1 MPa). The catalyst composition was prepared in a drybox by mixing together (t-butylamido)dimethyl(η$^5$-tetramethylcyclopentadienyl)titanium (η$^4$-1,3-pentadiene) catalyst, di(hydrogenated-tallowalkyl)methylammonium tris(pentafluorophenyl)phenylborate and (triisobutylaluminum modified methylalumoxane (MMAO) to give atomic ratios of B/Ti of 1.5/1 and of Al/Ti of 10/1. This mixture was then transferred to an addition loop and injected into the reactor. The polymerization was allowed to proceed for 10 minutes while feeding ethylene on demand to maintain a pressure of 450 psig. (3.1 MPa). The polymer solution was transferred from the reactor into a glass kettle and dried in a vacuum oven at 120° C. for about 16 hours. Efficiency was 0.6 (Kg polymer/g Ti metal).

EXAMPLE 4

Preparation of di(docosyl)methylammonium tetrakis (pentafluorophenyl)borate ($C_{22}H_{45}$)$_2$(CH$_3$)NH B($C_6F_5$)$_4$ ($C_{22}H_{45}$)$_2$(CH$_3$)NH B($C_6F_5$)$_4$ (ARMEEN® M2HE obtained from Akzo Nobel) (3.87 g, 5.97 mmol) was dissolved in 40 mL of hexane. Aqueous HCl (1 M, 5.97 mL) was added by syringe, resulting in the formation of a white precipitate. The mixture was placed on a mechanical shaker and shaken vigorously for 30 minutes, then LiB($C_6F_5$)$_4$ (4.30 g, 6.27 mmol) in a mixture of 30 mL of water and 20 mL of hexane was added. The mixture was shaken for another 30 minutes. It was then poured into a separatory funnel and the aqueous layer was removed. The organic layer was washed twice with 30 mL of saturated aqueous NaCl followed by two water washes. The organic layer was dried over MgSO$_4$. The mixture was then filtered through a glass frit (10–15 μm) to give a clear pale brown solution. The solution was transferred to a bottle, sparged thoroughly with nitrogen, and taken into the drybox. The hexane was removed under vacuum to give a solid residue. This residue was triturated with 10 mL of pentane to yield a pale brown solid. This solid was re-dissolved in 35–40 mL of Isopar E, and the concentration of this solution was measured gravimetrically to be 18.0 weight percent.

Polymerization

Substantially repeating the polymerization conditions of Example 1 using 1444 g mixed alkanes solvent, 124 g 1-octene comonomer, 1.0 μmol of (t-butylamido)dimethyl (η$^5$-tetramethylcyclopentadienyl)titanium (η$^4$-1,3-pentadiene) catalyst, 1.0 μmol di(docosyl)methylammonium tetrakis(pentafluoro-phenyl)borate cocatalyst and 10 μmole methylalumoxane scavenger resulted in the formation of ethylene/1-octene copolymer with an efficiency of 3.2 Kg polymer/g Ti.

What is claimed is:

1. A catalyst activator comprising a cation which is a Bronsted acid capable of donating a proton, and an inert, compatible, noncoordinating, anion, characterized by a solubility at 25° C. in hexane, cyclohexane or methylcyclohexane of at least 5 weight percent said activator having the formula: [L*–H]$^+$A$^-$, wherein:

L* is a nitrogen, sulfur or phosphorus containing Lewis base comprising from 1 to 3 C$_{10-40}$ alkyl groups with a total of from 12 to 100 carbons; and A$^-$ is a noncoordinating anion.

2. A catalyst activator comprising a cation which is a Bronsted acid capable of donating a proton, and an inert, compatible, noncoordinating, anion, characterized by a solubility at 25° C. in hexane, cyclohexane or methylcyclohexane of at least 5 weight percent said activator having the formula: [L*–H]$_d^+$A$^{d-}$, wherein:

L* is a nitrogen, sulfur or phosphorus containing Lewis base comprising from 1 to 3 C$_{10-40}$ alkyl groups with a total of from 12 to 100 carbons;

(L*-H)$^+$ is a Bronsted acid;

A$^{d-}$ is selected from the group consisting of:

A) sterically shielded diboron anions corresponding to the formula:

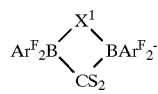

wherein:
S is alkyl, fluoroalkyl, aryl, or fluoroaryl (and where two S groups are present additionally hydrogen),
$Ar^F$ is fluoroaryl, and
$X^1$ is either hydrogen or halide and B) anions corresponding to the formula: $[M'^{k+}Q_{n'}]^{d-}$, wherein:
k is an integer from 1 to 3;
n' is an integer from 2 to 6;
n'−k=d;
M' is an element selected from Group 13 of the Periodic Table of the Elements; and
Q independently each occurrence is selected from hydride, dialkylamido, halide, alkoxide, aryloxide, hydrocarbyl, and halosubstituted-hydrocarbyl radicals, said Q having up to 20 carbons with the proviso that in not more than one occurrence is Q halide; and d is an integer from 1 to 3.

3. A catalyst activator according to claim 2 wherein the Lewis base comprises 2 $C_{10-40}$ alkyl groups and from 21 to 90 total carbons.

4. A catalyst activator according to claim 2 which is di(octadecyl)methylammonium tetrakis(pentafluorophenyl) borate, or di(hydrogenated-tallowalkyl)methylammonium tetrakis(pentafluorophenyl)borate.

5. A catalyst activator having the formula: $(L^*-H)^+ (BQ'_4)^-$; wherein,
L* is a nitrogen, sulfur or phosphorus containing Lewis base comprising 2 $C_{10-40}$ alkyl groups with a total of from 21 to 90 carbons;
B is boron in an oxidation state of 3; and
Q' is a fluorinated $C_{1-20}$ hydrocarbyl group.

6. A catalyst activator according to claim 5 wherein Q' is in each occurrence a fluorinated aryl group.

7. A catalyst activator according to claim 6 wherein Q' is in each occurrence a pentafluorophenyl group.

* * * * *

UNITED STATES PATENT AND TRADEMARK OFFICE
CERTIFICATE OF CORRECTION

PATENT NO : 5,919,983

DATED : July 6, 1999

INVENTOR(S) : Robert K. Rosen et al.

It is certified that error appears in the above-identified patent and that said Letters Patent is hereby corrected as shown below:

Column 2, line 43, "$(L*-H)_d+(A^{d-})$" should correctly read --$[L*-H]^+_d\ A^{d-}$--.

Column 2, line 46, "$(L*-H)^+$" should correctly read --$[L*-H]^+$--.

Column 6, line 5, delete the present drawing and insert therefor:

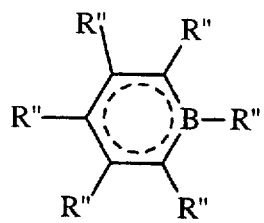

Column 14, line 26, "0.0075" should correctly read --0.0584--.

Column 17, line 61, "(triisobutylaluminum" should correctly read --triisobutylaluminum--.

Column 18, line 59, "$[L*-H]_d+A^{d-}$" should correctly read --$[L*-H]^+_dA^{d-}$--.

Signed and Sealed this

Twenty-fourth Day of October, 2000

Attest:

Q. TODD DICKINSON

*Attesting Officer*    *Director of Patents and Trademarks*